(12) United States Patent
Björling et al.

(10) Patent No.: US 8,738,120 B2
(45) Date of Patent: May 27, 2014

(54) IMPLANTABLE MEDICAL DEVICE AND METHOD COMPRISING MEANS FOR DETECTING AND CLASSIFYING AN ARRHYTHMIA

(75) Inventors: Anders Björling, Solna (SE); Malin Hollmark, Solna (SE); Tomas Svensson, Stockholm (SE); Stefan Hjelm, Bålsta (SE); Kjell Norén, Solna (SE); Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 1 day.

(21) Appl. No.: 13/696,261

(22) PCT Filed: May 12, 2010

(86) PCT No.: PCT/SE2010/050527
§ 371 (c)(1),
(2), (4) Date: Nov. 5, 2012

(87) PCT Pub. No.: WO2011/142702
PCT Pub. Date: Nov. 17, 2011

(65) Prior Publication Data
US 2013/0060118 A1    Mar. 7, 2013

(51) Int. Cl.
*A61B 5/0468* (2006.01)

(52) U.S. Cl.
USPC ............................ 600/515; 600/512; 600/513

(58) Field of Classification Search
CPC ............. A61B 5/0452; A61B 5/04011; A61B 5/04525; A61B 5/0205; A61B 5/0002; G06F 19/345; G06F 19/322
USPC .......... 600/508, 509, 512, 513, 515; 706/924; 128/920, 923
See application file for complete search history.

(56) References Cited

U.S. PATENT DOCUMENTS

| 2007/0005114 A1 | 1/2007 | Salo et al. |
| 2007/0043394 A1 | 2/2007 | Zhang et al. |
| 2007/0078356 A1 | 4/2007 | Faber et al. |
| 2008/0097539 A1 | 4/2008 | Belalcazar et al. |
| 2009/0264716 A1 | 10/2009 | Shuros et al. |

FOREIGN PATENT DOCUMENTS

| WO | 2008118349 A1 | 2/2008 |
| WO | 2008153450 A1 | 12/2008 |
| WO | 2009082284 A1 | 7/2009 |
| WO | 2009096819 A1 | 8/2009 |

OTHER PUBLICATIONS

Intern'l Search Report—PCT/SE2010/050527, mailed Jan. 19, 2011.

*Primary Examiner* — Christopher D Koharski
*Assistant Examiner* — Michael Carey

(57) ABSTRACT

An implantable medical device (100) is configured for generating a cardiogenic impedance signal representative of the cardiogenic impedance of at least a portion of a heart (10) of a subject (20) during at least a portion of cardiac cycle. A moment processor (132) calculates a moment parameter value based on the cardiogenic impedance signal. The moment parameter is representative of a weighted sum of impedance amplitudes within a time window centered at defined time instance within the cardiac cycle. The weights of the impedance amplitudes are further dependent on the length in time between the defined time instance and the point of time of the associated impedance amplitude. The moment parameter is of high diagnostic value and is employed by an arrhythmia classifier (132) in order to classify a detected arrhythmia of the heart (10), such as discriminate between hemodynamically stable or unstable arrhythmias and/or supraventricular or ventricular tachycardia.

21 Claims, 6 Drawing Sheets

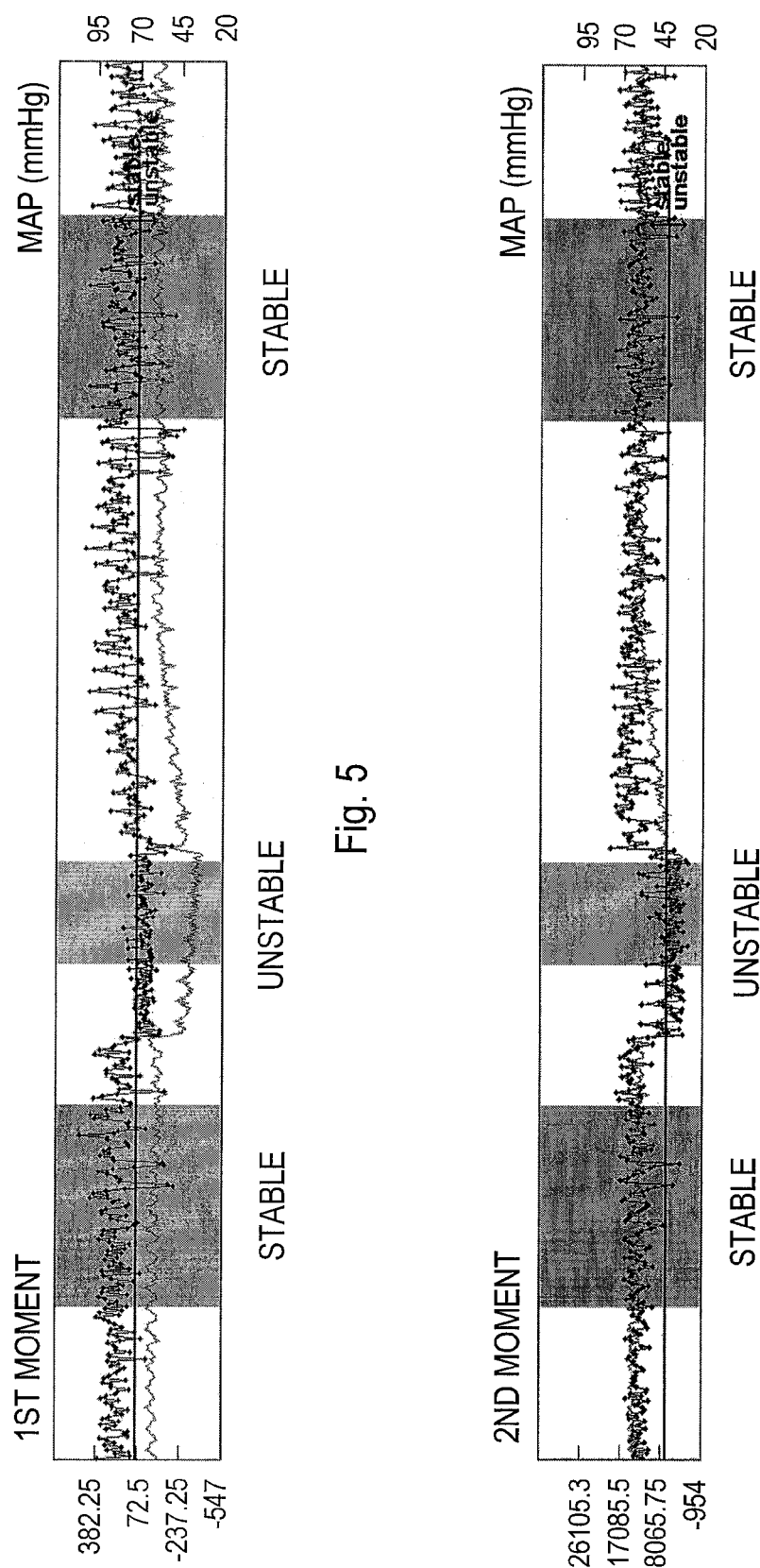

IMPLANTABLE MEDICAL DEVICE AND METHOD COMPRISING MEANS FOR DETECTING AND CLASSIFYING AN ARRHYTHMIA

TECHNICAL FIELD

The present invention generally relates to arrhythmia classification, and in particular to an implantable medical device capable of detecting and classifying an arrhythmia and to an arrhythmia classification method.

BACKGROUND

Implantable medical devices (IMDs), including implantable cardioverter-defibrillators (ICDs) and pacemakers, can today be used for detecting and combating arrhythmias, such as ventricular tachyarrhythmia in IMD patients. Ventricular tachyarrhythmias, for example ventricular fibrillation or tachycardia, need to be detected as early as possible as they may otherwise lead to the death of the patient if not quickly terminated. As a consequence, once tachyarrhythmia is detected, the IMD will combat it by delivering one or more defibrillation or cardioversion shocks.

However, in several IMD and ICD patients about 5-15% of the defibrillation or cardioversion shocks are in fact unnecessary. This means that worst-case approximately one shock out of five is inappropriate for these patients. Inappropriate shocks cause decreased quality of life for the patients, battery depletion of the device and potential induction of dangerous arrhythmias. Inappropriate shocks should therefore be minimized.

The document U.S. Pat. No. 5,311,874 discloses a method for tachycardia discrimination. In a first embodiment, a cardiac biopotential signal is recorded and processed to identify a number of feature values representing maximum and minimum values of a complex in the signal, corresponding to a complete cardiac cycle. Firstly, the complex is classified as a baseline complex or a non-baseline complex based on the cycle length of the complex. If the complex is classified as a non-baseline complex, an extensive and very complex processing of its feature values is conducted to subsequently arrive at a discrimination point in a plane defined by a similarity vector and a dissimilarity vector. Depending on where this point is in the plane, the non-baseline complex is classified as a ventricular tachycardia (VT) or non-VT complex. In a second embodiment, a corresponding complex signal processing is performed but for discriminating between hemodynamically stable and unstable ventricular tachycardias. In this case, the input signal can be a signal or condition related to the hemodynamics of the heart, such as pressure, flow or impedance.

The document US 2005/0154421 discloses a technique for reducing inappropriate delivery of therapy to treat ventricular tachyarrhythmias caused by supraventricular tachycardia (SVT). The document specifies that SVT can be conducted to the ventricles and lead to short ventricular cycle lengths (VCLs) that would imply ventricular tachyarrhythmia. Their technique is based on measuring multiple VCLs over a defined time period. The number of such cycles that have a length shorter than a given threshold is determined and used as a basis for detecting ventricular tachyarrhythmia. If tachyarrhythmia is detected, it is determined whether the tachyarrhythmia is due to SVT or may indeed be lethal. This determination can be based on measured VCLs and atrial cycle lengths (ACLS), measured activity level of the patient or intracardiac pressure measurements.

US 2007/0043394 discloses an IMD having circuitry for sensing cardiac signals and determining an intracardiac impedance signal. Cardiac cycles of a subject are determined based on the sensed cardiac signal and tachyarrhythmia is detected using cardiac cycle to cardiac cycle changes in a plurality of intracardiac impedance parameters obtained from the intracardiac impedance signal.

U.S. Pat. No. 5,779,645 disclosed discrimination between ventricular tachycardia and a sinus tachycardia or a supraventricular tachycardia. A template based on morphology of a normal sinus rhythm is collected. A test signal is compared against the template to determine how closely the test and template signals correspond based on morphology. The comparison is done based on peak information in the template and the test signal. A score is generated to indicate the degree of similarity between the template and the test signal.

There is still a need for a technique and IMD capable of accurately classifying arrhythmias in order to select appropriate treatments or select not to apply any combating treatment to the subject.

SUMMARY

It is an objective to enable classification of arrhythmias of a patient.

It is a particular objective to provide an implantable medical device capable of classifying detected arrhythmias.

These and other objectives are met by embodiments as disclosed herein.

Briefly, an embodiment relates to an implantable medical device (IMD) designed to deliver cardiac therapy to a patient's heart. The IMD comprises an electrode connector that is electrically connectable to multiple electrodes of which at least one is provided on a cardiac lead that can be connected to the electrode connector and the IMD. A signal generator of the IMD is connected to the electrode connector and is configured to generate an electric signal that is to be applied over connectable electrodes. A signal sensing unit is configured to sense the resulting electric signal over two connectable electrodes. The applied electric signal and the sensed resulting electric signals are processed by an impedance processor of the IMD. The impedance processor in particular determines a cardiogenic impedance signal representative of the cardiogenic impedance over at least a portion of the patient's heart for at least a portion of a cardiac cycle. A moment processor processes the cardiogenic impedance signal for the purpose of calculating a moment parameter value. This moment parameter is representative of a weighted sum of impedance amplitudes within a time window centered at a defined time instance corresponding to the timing of a defined cardiac event within the cardiac cycle. The weights and in particular the magnitudes of the weights for the impedance amplitude values are further dependent on the length in time between the defined time instance and the point in time for the impedance amplitude to be multiplied by the particular weight. The weights are preferably signed weights where the sign of a weight depends on whether the point in time for the impedance amplitude occurs prior or after the defined time instance. The calculated moment parameter is of high diagnostic value and is used by an arrhythmia classifier of the IMD to classify an arrhythmia of the heart in order enable selection and application of appropriate anti-arrhythmia treatment if at all needed.

An aspect of the embodiments relate to a method of classifying an arrhythmia of a patient's heart and involves applying an electric signal over a portion of the heart and sensing a resulting electric signal over a portion of the heart. A cardiogenic impedance signal is determined based on the applied electric signal and the sensed resulting electric signal. The method also comprises calculating a moment parameter value based on the cardiogenic impedance signal and employing the moment parameter for classifying an arrhythmia of the heart.

The embodiments enable an efficient and reliable classification of arrhythmia events by the IMD itself once these events occur. The IMD can thereby decide on the most appropriate treatment scheme to put in based on the particular arrhythmia class of the event as determined based on the moment parameter.

BRIEF DESCRIPTION OF THE DRAWINGS

The invention, together with further objects and advantages thereof, may best be understood by making reference to the following description taken together with the accompanying drawings, in which:

FIG. 3 is an illustration of a lead configuration applicable according to an embodiment;

FIG. 5 schematically illustrates a moment parameter representing the first moment and mean arterial pressure (MAP) over time for a porcine suffering from various forms of arrhythmias as recorded with a right atrial ring—left ventricular ring bipolar impedance vector;

FIG. 6 schematically illustrates a moment parameter representing the second moment and mean arterial pressure (MAP) over time for a porcine suffering from various forms of arrhythmias as recorded with a right ventricular tip—right ventricular ring bipolar impedance vector;

DETAILED DESCRIPTION

Figure 1:
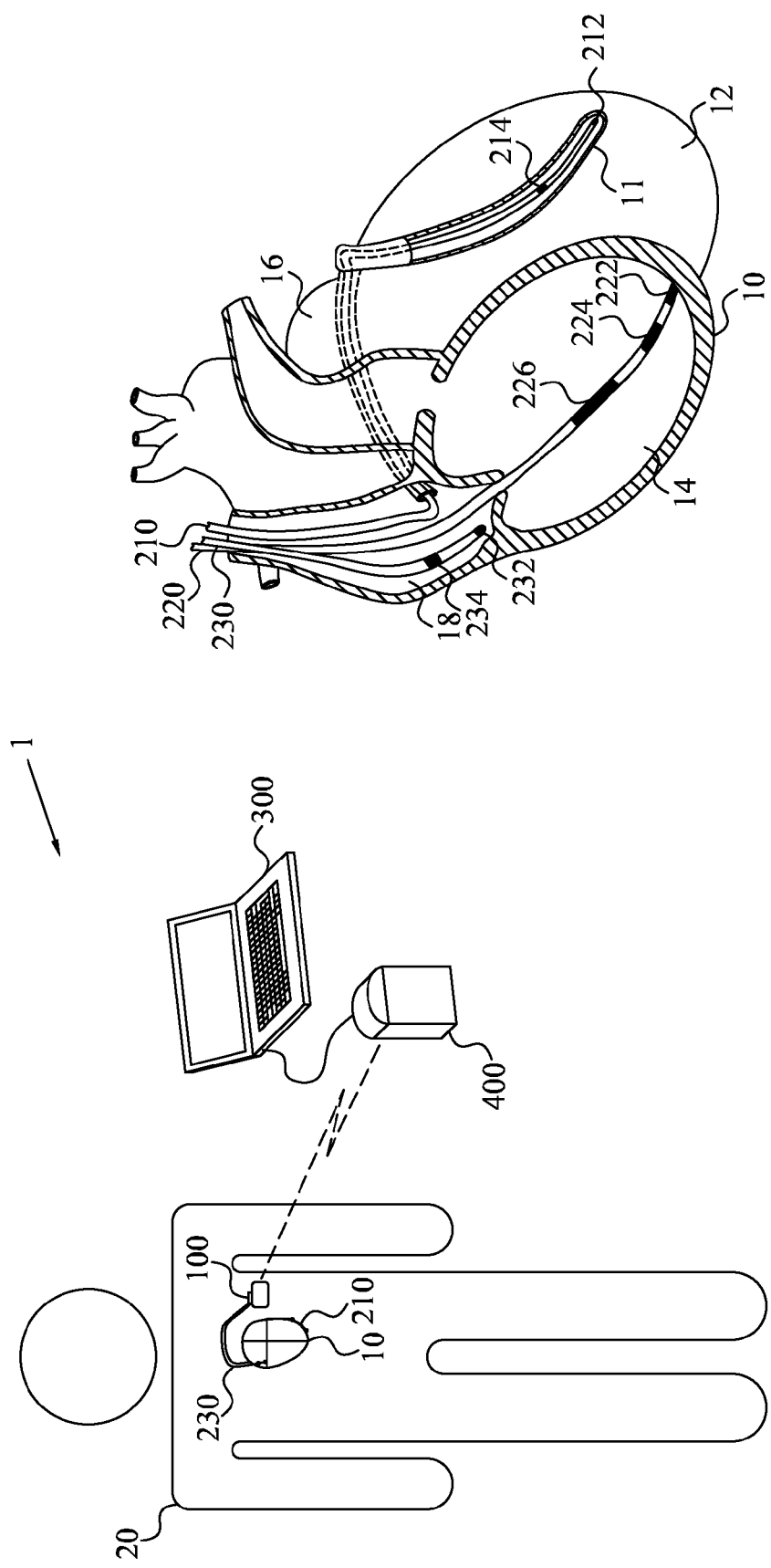
FIG. 1 is a schematic overview of an implantable medical device in a human subject and a non-implantable data processing unit capable of conducting wireless communication with the implantable medical device.

Throughout the drawings, the same reference numbers are used for similar or corresponding elements.

The present invention generally relates to arrhythmia classification and in particular to implantable medical devices and methods capable of classifying an arrhythmia of a patient's heart and thereby provide relevant diagnostic information that can be useful in selecting an appropriate treatment scheme to combat the arrhythmia.

Arrhythmia or cardiac dysrhythmia is a large and heterogeneous group of conditions in which there is abnormal electrical activity in the heart. For instance, the heart may beat too fast or too slow, and may be regular or irregular. There is therefore a need for a technique that allows discrimination and classification between different forms of arrhythmia to thereby select the most appropriate treatment scheme to combat a detected and classified arrhythmia.

For instance, ventricular tachyarrhythmia relates to medical conditions in which the electrical activity of the heart is irregular and/or faster than normal and where the abnormal activity originates from or is caused by the left and/or right ventricle. Ventricular tachyarrhythmias are traditionally defined as ventricular tachycardia, ventricular flutter and ventricular fibrillation.

Ventricular tachycardia is a potentially life threatening cardiac tachyarrhythmia originating in the ventricles. The tachycardia is characterized by increased heart rate, often in the interval of 120 to 250 beats per minutes. It may degrade into the more serious ventricular fibrillation.

Ventricular flutter is a ventricular tachyarrhythmia characterized electrocardiographically by smooth undulating waves with QRS complexes merged with T waves, and a rate of approximately 250 beats per minute. If untreated it usually progresses to ventricular fibrillation.

Ventricular fibrillation is a condition with uncoordinated contraction of the cardiac muscle of the ventricles in the heart. As a result, the heart fails to adequately pump the blood and hypoxia may occur. If continuing for more than a few seconds, blood circulation and blood pressure will drop significantly.

Ventricular flutter and fibrillation should, typically, be treated immediately with a defibrillation shock. However, for other types of ventricular tachyarrhythmias it might be sufficient to use an anti-tachycardia pacing (ATP) scheme in order to combat the ventricular tachyarrhythmia and no shock is needed. An ATP-based treatment scheme is generally preferred from the patient point of view as inappropriate shocks are unpleasant to the patient and further drains power from the battery of the ICD.

In an embodiment, an arrhythmia classification differentiates between so called hemodynamically stable arrhythmias, such as stable ventricular tachyarrhythmias, and hemodynamically unstable arrhythmias, such as unstable ventricular tachyarrhythmias. Stable and unstable arrhythmias are also denoted non-hemodynamically and hemodynamically compromising arrhythmias in the art, respectively.

For instance, a hemodynamically stable form of ventricular tachyarrhythmias is typically characterized by stable blood pressure or only temporarily and slightly decreasing (typically less than 20%, preferably less than 10%, such as less than 5% or less than 1%) blood pressure. However, lethal and unstable forms of ventricular tachyarrhythmias, in clear contrast, lead to large drops in blood pressure, typically with about or even more than 50%. In severe conditions, the systolic blood pressure could even fall as low as 50 mmHg or even lower.

In another embodiment, the arrhythmia classification can be performed in order to discriminate between supraventricular tachyarrhythmias (SVTs) and ventricular tachyarrhtyhmias (VTs). An SVT is a tachycardiac rhythm originating above the atrioventricular valve plane. The SVT can be from a sinoatrial source, an atrial source or an atrioventricular source. In contrast to VTs, SVTs can often be left without any shocking. Thus, the treatment scheme for a classified SVT most often differ from the treatment scheme that is most appropriate for a classified VT.

The above listed embodiments of arrhythmia classification, i.e. based on a hemodynamic assessment or based on the origin of the arrhythmia, should be seen as preferred but non-limiting examples of different arrhythmia types or classes that can be identified by the embodiments. In the following these examples will be employed to illustrate different embodiments of the invention.

FIG. 1 is schematic overview of a system 1 comprising an implantable medical device (IMD) 100 according to the embodiments and a non-implantable data processing device 300. In the figure, the IMD 100 is illustrated implanted in a human patient 20 and as a device that monitors and/or provides therapy to the heart 10 of the patient 20. The patient 20 must not necessarily be a human patient but can instead be an animal patient, in particular a mammalian patient, in which an IMD 100 can be implanted. The IMD 100 can be in the form of a pacemaker, cardiac defibrillator or cardioverter, such as implantable cardioverter-defibrillator (ICD). The IMD 100 is, in operation, connected to one or more, two in the figure, cardiac leads 210, 230 inserted into different heart chambers, the right atrium and left ventricle in the figure, or elsewhere provided in connection with a heart chamber.

The figure also illustrates an external data processing device 300, such as programmer or clinician's workstation, that can communicate with the IMD 100, optionally through a communication device 400 that operates similar to a base station on behalf of the data processing device 300. As is well known in the art, such a data processing device 300 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the data processing device 300 before display to a clinician. In the light of the present invention, such diagnostic data can include cardiogenic impedance data or moment parameter data generated by the IMD 100, arrhythmia classification data and/or other diagnostic data relating to arrhythmia detection and classification.

Figure 2:
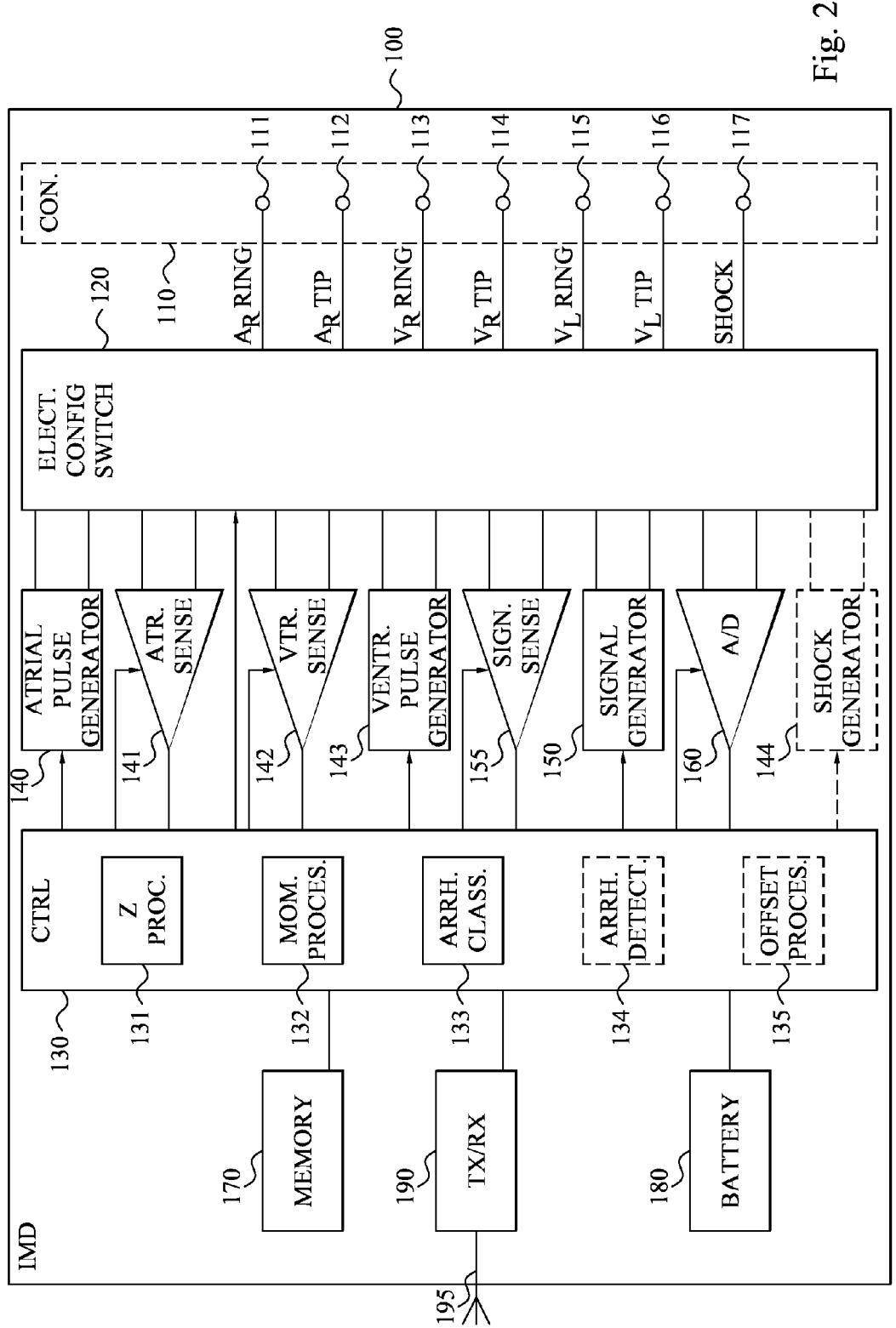
FIG. 2 is a block diagram of an embodiment of an implantable medical device.

FIG. 2 illustrates an embodiment of an IMD 100 suitable for delivering cardiac therapy to a heart of a subject. The figure is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination to provide an IMD capable of treating the appropriate heart chamber(s) with pacing stimulation and also cardioversion and/or defibrillation.

The IMD 100 comprises a housing, often denoted as can or case in the art. The housing can act as return electrode for unipolar leads, which is well known in the art. The IMD 100 also comprises an electrode connector or input/output (I/O) 110 having, in this embodiment, a plurality of terminals 111-117. With reference to FIGS. 2 and 3, the lead connector 110 is configured to be, during operation in the subject body, electrically connectable to, in this particular example, a right atrial lead 230, a left ventricular lead 210 and a right ventricular lead 220. The electrode connector 110 consequently comprises terminals 111, 112 that are electrically connected to matching electrode terminals of the atrial lead 230 when the atrial lead 230 is introduced in the lead connector 110. For instance, one of these terminals 112 can be designed to be connected to a right atrial tip terminal of the atrial lead 230, which in turn is electrically connected through a conductor running along the lead body to a tip electrode 232 present at the distal end of the atrial lead 230 in the right atrium 18 of the heart 10. A corresponding terminal 111 is then connected to a right atrial ring terminal of the atrial lead 230 that is electrically connected by another conductor in the lead body to a ring electrode 234 present in connection with the distal part of the atrial lead 230, though generally distanced somewhat towards the proximal lead end as compared to the tip electrode 232.

In an alternative implementation, the IMD 100 is not connectable to a right atrial lead 230 but instead to a left atrial lead configured for implantation in the left atrium 16. A further possibility is to have an IMD 100 with an electrode connector 110 having sufficient terminals to allow the IMD 100 to be electrically connectable to both a right atrial lead 230 and a left atrial lead. Though, it is generally preferred to have at least one electrically connectable atrial lead in order to enable atrial sensing and pacing, the IMD 100 does not necessarily have to be connectable to any atrial leads. In such a case, the terminals 111, 112 of the electrode connector 110 can be omitted.

In order to support right chamber sensing and pacing, the lead connector 110 further comprises a right ventricular tip terminal 114 and a right ventricular ring terminal 113, which are adapted for connection to a right ventricular tip electrode 222 and a right ventricular ring electrode 224 of the right ventricular lead 220 implantable in the right ventricle 14, see FIG. 3.

In an alternative embodiment, the lead connector 110 is instead or also connectable to a left ventricular lead 210. A left ventricular lead 210 is typically implanted in the coronary venous system 11 for safety reasons although implantation inside the left ventricle 12 has been proposed in the art. In the following, "left ventricular lead" 210 is used to describe a cardiac lead designed to provide sensing and pacing functions to the left ventricle 12 regardless of its particular implantation site, i.e. inside the left ventricle 12 or in the coronary venous system 11. The left ventricular lead 210 preferably also comprises a tip electrode 212 and a ring electrode 214 electrically connectable to corresponding terminals 115, 116 of the electrode connector 110.

The electrode connector 110 preferably also comprises a terminal 117 configured to be electrically connectable to a shock electrode 226 preferably provided on the right atrial lead 220, the left ventricular lead 210 or the right atrial lead 230. The electrode connector 110 can alternatively have multiple terminals 117 configured to be electrically connectable to multiple shock electrodes, if more than one of the connectable leads 210, 220, 230 is equipped with such a shock electrode 226 configured to deliver a defibrillation/cardioversion shock.

Any of the right ventricular lead 220 and the left ventricular lead 210 can be a so-called multi-electrode ventricular lead. In such a case, the lead generally has multiple ring electrodes provided at different positions along the lead. The electrode connector 110 then has to have appropriate number of terminals for electrical connection to these multiple electrodes.

The housing can act as return electrode as mentioned above. In such a case, the electrode connector 110 can have a dedicated terminal (not illustrated) connected to the housing.

The IMD 100 as illustrated in FIG. 2 comprises an optional atrial pulse generator 140 and an optional ventricular pulse generator 143 that generate pacing pulses for delivery by the atrial lead(s) and the ventricular lead(s) preferably through an electrode configuration switch 120.

It is understood that in order to provide stimulation therapy in different heart chambers, the atrial and ventricular pulse generators 140, 143 may include dedicated, independent pulse generators, multiplexed pulse generators, or shared pulse generators. The pulse generators 140, 143 are controlled by a controller 130 via appropriate control signals, respectively, to trigger or inhibit the stimulating pulses.

The IMD 100 also comprises the controller 130, preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signal as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

The controller 130 further controls the timing of the stimulating pulses, such as pacing rate, atrioventricular interval (AVI), atrial escape interval (AEI) etc. as well as to keep track of the timing of refractory periods, blanking periods, noise detection windows, evoked response windows, alert intervals, marker channel timing, etc.

A preferred electronic configuration switch 120 includes a plurality of switches for connecting the desired terminals 111-117 to the appropriate I/O circuits, thereby providing complete electrode programmability. Accordingly, the electronic configuration switch 120, in response to a control signal from the controller 130, determines the polarity of the stimulating pulses (e.g., unipolar, bipolar, combipolar, etc.) by selectively closing the appropriate combination of switches (not shown) as is known in the art.

An optional atrial sensing circuit or detector 141 and an optional ventricular sensing circuit or detector 142 are also selectively coupled to the atrial lead(s) and the ventricular lead(s) through the switch 120 for detecting the presence of cardiac activity in the heart chambers. Accordingly, the atrial and ventricular sensing circuits 141, 142 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 141, 142 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 141, 142 are connected to the controller 130, which, in turn, is able to trigger or inhibit the atrial and ventricular pulse generators 140, 143, respectively, in a demand fashion in response to the absence or presence of cardiac activity in the appropriate chambers of the heart.

Furthermore, the controller 130 is also capable of analyzing information output from the sensing circuits 141, 142 and/or a data acquisition unit 160 to determine or detect whether and to what degree tissue capture has occurred and to program a pulse, or pulse sequence, in response to such determinations. The sensing circuits 141, 142, in turn, receive control signals over signal lines from the controller 130 for purposes of controlling the gain, threshold, polarization charge removal circuitry, and the timing of any blocking circuitry coupled to the inputs of the sensing circuits 141, 142 as is known in the art.

According to the embodiments cardiac signals are applied to inputs of a data acquisition unit 160 connected to the electrode connector 110. The data acquisition unit 160 is preferably in the form of an analog-to-digital (ND) data acquisition unit 160 configured to acquire intracardiac electrogram (IEGM) signals, convert the raw analog data into a digital signal, and store the digital signals for later processing and/or transmission to the programmer by a transceiver 190. The data acquisition unit 160 is coupled to the atrial lead and/or the ventricular lead through the switch 120 to sample cardiac signals across any pair of desired electrodes.

The IMD 100 also comprises a signal generator 150 connectable to two of the terminals 111-117 preferably through the switch 120. The signal generator 150 is configured to generate an electric signal that is applicable over two electrodes arranged in connection with the patient's heart. Thus, the generated electric signal is forwarded by the switch 120 to two of the terminals 111-117 and further to the corresponding electrodes connectable to the selected terminals.

The electric signal is preferably an AC current having a defined time-dependent voltage/current profile. The electric signal is preferably a sub-threshold electric signal implying that it is not intended to trigger capture of the myocardium when applied to the heart. This is in clear contrast to the pacing pulses generated by the atrial 140 and ventricular 143 pulse generator.

In the figure the signal generator 150 has been illustrated as a stand-alone signal generator 150 controlled by the controller 130. In an alternative approach, the relevant sub-threshold AC signal could instead be generated by the atrial 140 or ventricular 143 pulse generator, thereby relaxing the need for a further generator 150 of the IMD 100. In such a case, the controller 130 controls the atrial 140 or ventricular 143 pulse generator to generate the electric signal having characteristics, i.e. duration and amplitude, which generally differ from the pacing pulses otherwise generated by the pulse generator 140, 143.

A signal sensing unit 155 is implemented preferably connected to the switch 120 and thereby to two electrode terminals connected to two electrodes. The sensing unit 155 is configured to sense a resulting electric signal captured over the two electrodes. The resulting electric signal is preferably a resulting AC signals originating from at least a portion of the heat. This sensed AC signals is further generated due to the applied AC signal generated by the signal generator 150.

An impedance processor 131 is implemented in the IMD 100 and configured to determine a cardiogenic impedance signal of the heart for at least a portion of a cardiac cycle based on the electric signal generated by the signal generator 150 and the resulting electric signal sensed by the signal sensing unit 155. In a particular embodiment, the impedance processor 131 generates the cardiogenic impedance signal based on the current of the electric signal and the measured or sensed voltage of the resulting electric signals according to techniques well known in the art. The cardiogenic impedance signal is representative of the impedance as measured over a portion of the heart during a cardiac cycle, during multiple cardiac cycles or during a portion of the cardiac cycle as is further described herein.

In a particular embodiment, the impedance processor 131 determines the cardiogenic impedance signal as a bandpassed version of the calculated impedance signal in order to remove or at least suppress the respiratory contribution to the impedance signal. The cardiogenic impedance signal is further preferably characterized by not having any DC component, i.e. its average value is zero.

As known in the art, bipolar, tripolar or quadropolar impedance signals can be determined. In a bipolar setting the same pair of electrodes is used by both the signal generator 150 for signal application as for the signal sensing unit 155 for sensing the resulting electric signals. Bipolar impedance signals are in particular reflective of the local environment around the electrodes. Tripolar settings have a common electrode between signal application and signal sensing, whereas quadropolar settings use two electrodes for signal application and two other electrodes for signal sensing. Tripolar and quadropolar impedance signals are more reflective of global properties affecting the impedance as compared to the bipolar impedance signals.

Animal experiments have been conducted with various impedance vectors and settings. The impedance vectors that was determined to be best suited to differentiate the various arrhythmias can be selected among right ventricular (RV) tip—RV ring bipolar, right atrial (RA) ring—left ventricular (LV) ring bipolar, RA—RV tripolar (current: RA tip—RV ring; voltage RA ring—RV ring), RA tip—RA ring bipolar, RV—case tripolar (current: RV tip—case; voltage RV ring—case), RV tip—RV coil bipolar and RV—LV quadropolar (current: RV tip—LV tip; current: RV ring—LV ring). These bipolar, tripolar and quadropolar settings work well. The embodiments are though not limited to these particular impedance configurations but can be applied to other bipolar, tripolar and quadropolar configurations.

The IMD 100 also comprises a moment processor 132 configured to process the cardiogenic impedance signal determined by the impedance processor 131 in order to calculate a moment parameter that has diagnostic value in terms of enabling classification of an arrhythmia of the heart. The moment processor 132 in particular calculates a moment parameter value based on the cardiogenic impedance signal. This moment parameter is representative of a weighted sum of impedance amplitudes within a time window. This time window is further encompassed by the at least a portion of the cardiac cycle and is centered at a defined time instance within the at least a portion of the cardiac cycle. The time window thereby defines a portion of the cardiac cycle and the cardiogenic impedance signal present within this portion of the cardiac cycle. By centering the time window at the defined time instance the relevant portion of the cardiogenic impedance signal that is employed by the moment processor 132 to calculate the moment parameter value precedes the defined time instance with half the length of the time window and continues up to half the length of the time window pas the defined time instance.

The weights employed by the moment processor 132 to calculate the weighted sum are dependent on the length in time between the defined time instance and the point in time for the impedance amplitude associated with the particular weight. This means that the weight of a given impedance amplitude reflects how much the point in time for the impedance amplitude precedes or is past the defined time instance.

As a consequence, an impedance amplitude of an impedance sample in the cardiogenic impedance signal being close to the start or the end of the time window thereby has a comparatively longer length in time to the defined time instance as compared to an impedance amplitude of an impedance sample being close to the defined instance and thereby close to the center of the time window.

In a preferred embodiment, the weight of an impedance amplitude is equal to the signed length in time between the defined time instance and the point in time for the impedance amplitude associated with the weight. This means that impedance amplitude values for impedance samples preceding the defined time instance preferably have negative weights whereas impedance samples occurring within the time window but following the defined time instance preferably have positive values for their weights. In addition, impedance samples close to the either end of the time window preferably have larger weight values as compared to impedance samples close to the midpoint of the time window and the defined time instance.

The cardiogenic impedance signal generated by the impedance processor 131 may be a complex valued impedance signal so that each impedance sample has a real value, Re, and an imaginary value, Im. In a particular embodiment, the impedance processor 131 generates the impedance amplitudes for the impedance samples of cardiogenic impedance signal within the time window as $|Re+iIm|=\sqrt{Re^2+Im^2}$. In an alternative embodiment, the cardiogenic impedance signal generated by the impedance processor 131 is not a complex valued impedance signal but merely comprises a real impedance value per impedance sample. This real impedance value of an impedance sample can then be utilized directly as impedance amplitude for that impedance sample without calculating any absolute value.

The relevant portion of the cardiogenic impedance signal in terms of constituting the basis for the calculation of the moment parameter is, thus, the impedance samples present within the time window centered at the defined time instance. This means that actually only these impedance samples of the cardiogenic impedance signal are needed. The signal generator 150 can therefore generate and apply the electric signal only during this time window. In such a case, the cardiogenic impedance signal will then only be determined for the time window. Alternatively, the signal generator 150 can generate and apply the electric signal during a longer period of time than the time window, possibly spanning over multiple consecutive cardiac cycles. However, in such a case and for a given cardiac cycle, the moment processor 132 preferably only processes the impedance samples of the cardiac impedance signal within the time window.

An arrhythmia classifier 133 is configured to use the moment parameter value as calculated by the moment processor 132 to classify an arrhythmia of the heart. Thus, the arrhythmia classification of the embodiments is based on the moment parameter as a diagnostic arrhythmia-classifying parameter.

Figure 4:
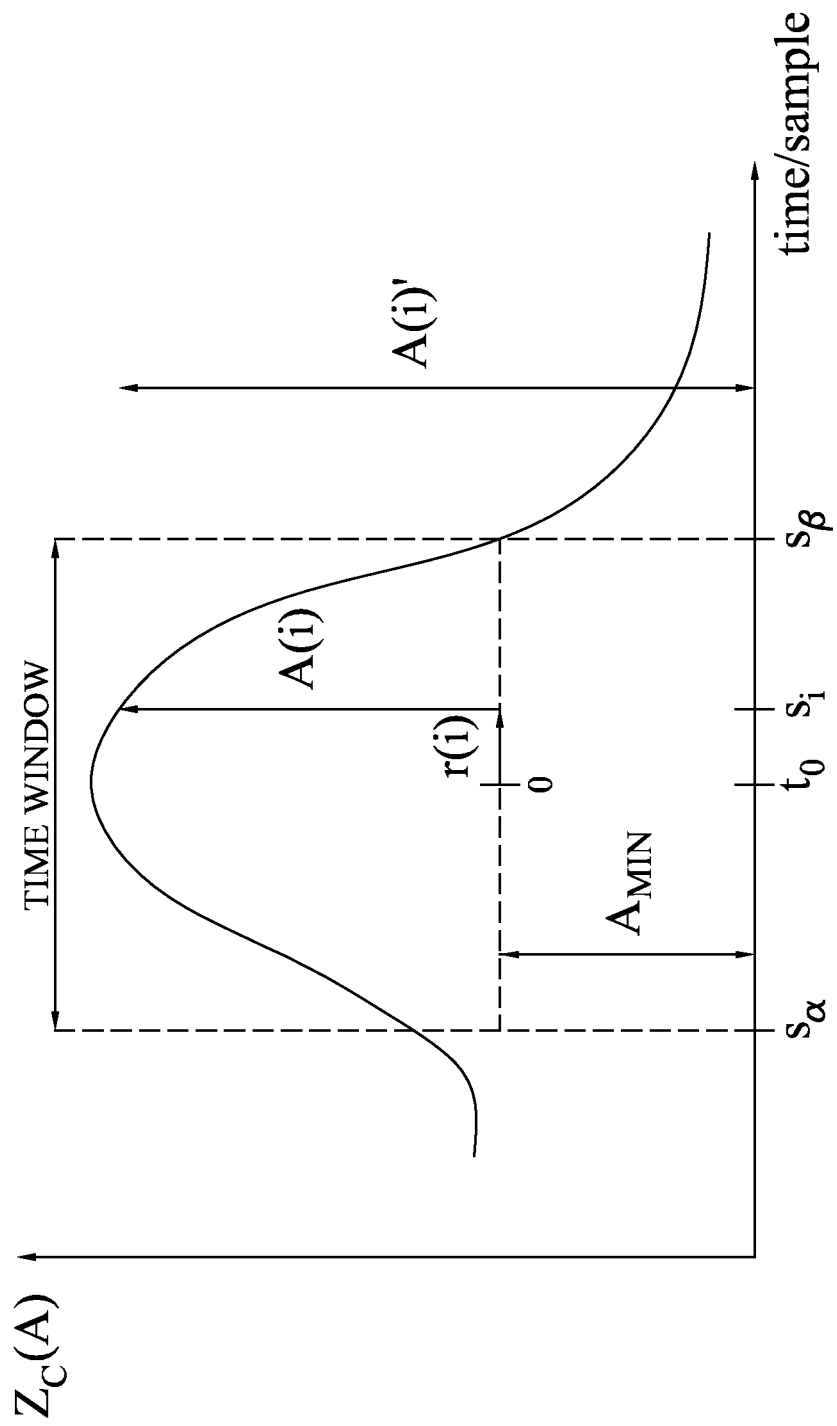
FIG. 4 schematically illustrates principles of calculating a moment parameter according to an embodiment.

FIG. 4 is a drawing illustrating a diagram of impedance amplitude values of the cardiogenic impedance signal ($Z_C$) during a portion of a cardiac cycle. In the figure, the defined time instance within the cardiac cycle is marked as $t_0$. The time window is also marked in the figure and is centered at the defined time instance. It is this part of the cardiogenic impedance signal, i.e. within the vertical hatched lines, that are employed by the moment processor 132 for calculating the moment parameter value.

In a general embodiment, the moment processor 132 is configured to calculate the moment parameter based on $$\sum_i r(i)^k \times A(i),$$

wherein r(i) represents the length in time between the defined time instance, $t_0$, and the point in time for impedance sample number i, $s_i$, of the cardiogenic impedance signal. A(i) represents the impedance amplitude for the impedance sample $s_i$, k is a positive integer and $i \in [\alpha, \beta]$, where $\alpha$ is the sample number of a first impedance sample, $s_\alpha$, within the time window and $\beta$ is the sample number of a last impedance sample, $s_\beta$, within said time window.

In particular embodiment the weight w(i) has a magnitude |r(i)$^k$|. The preferred sign of the weight w(i) is then dependent on whether the point in time for impedance sample number i occurs prior or after the defined time instance $t_0$. Thus, impedance samples prior the defined time instance then has negative (or positive) signs, whereas impedance samples after the defined time instance has positive (or negative) signs. The moment parameter is then determined based on $$\sum_i w(i) \times A(i).$$

Thus, in a particular embodiment the impedance processor 131 determines a cardiogenic impedance signal that comprises a respective impedance amplitude for at least each impedance sample within the portion of the cardiac cycle corresponding to the time window centered at the defined time instance. The cardiogenic impedance signal then comprises multiple impedance sample $s_i$ that each comprise a respective impedance amplitude value A(i).

Depending of the value of k various moment parameters are possible and within the scope of the embodiments. For instance, k=1 implies that the moment processor 132 calculates a moment parameter that is equal to or at least based on $$P = \sum_i r(i) \times A(i).$$

Such a moment parameter resembles the first moment or the moment of force within the field of mechanics. Correspondingly, if the moment processor 132 instead uses k=2 the moment parameter is equal to or based on $$P = \sum_i r(i)^2 \times A(i).$$

In such a case, the moment parameter resembles the second moment or the moment of inertia. A further possibility for moment parameter that can be calculated by the moment processor 132 is actually based on the first moment resembling parameter above and is normalized by the sum of impedance amplitude values within the time window to get a moment parameter that resembles the center of gravity:

$$P = \frac{\sum_i r(i) \times A(i)}{\sum_i A(i)}.$$

This latter embodiment of the moment parameter is indicative of how much the cardiogenic impedance signal is shifted—backwards or forwards in time—in relation to the defined time instance $t_0$. The cardiogenic impedance signal contains information of the mechanical activity of the heart during at least a portion of a cardiac cycle. This means that the impedance samples within the time window that precede the defined time instance $t_0$ represent the cardiac mechanical activity occurring prior to the defined time instance. Correspondingly, the impedance samples within the time window that follow the defined time instance reflect the cardiac mechanically activity occurring after the defined time instance.

As is well known in the art, the conductivity of blood is higher than the conductivity of the cardiac tissue. As a consequence, a high impedance amplitude value corresponds to low blood volume. The timing of such a high impedance amplitude value thereby corresponds to the time of low blood volume within a cardiac chamber and therefore the time of complete heart contraction if the cardiac chamber is a ventricle. This means that if the "center of gravity" is shifted forwards in time relative to the defined time instance (to the right in FIG. 4), the time of complete heart contraction is also shifted to the right, implying increased electromechanical delay. Any morphological changes in the cardiogenic impedance signal around the central defined time instance, thereby, causes a change in the value of the moment parameter embodiment resembling the center of gravity.

The moment parameter embodiment resembling the first moment depends on the size of the waveform of the cardiogenic impedance signal within the time window. This means that the moment parameter will change not only with morphological changes but also with changes in waveform size. This is advantageously since an arrhythmia event typically does not only cause changes in the cardiogenic impedance signal morphology but also in the impedance signal size. The embodiment of the moment parameter resembling the second moment places increased weight on the impedance signals further away from the central defined time instance. Thus, increase impedance amplitude far away from the midpoint will result in a greater change in this embodiment of the moment parameter than if the increased impedance amplitude was close to the midpoint.

The moment processor 132 may additionally determine the moment parameter based on one or multiple of the first moment parameter, the second moment parameter and the center of gravity parameter mentioned above. For instance, the moment parameter can be determined to be equal to the variation in one of these parameters, the mean or median of one of these parameters for a selected number of cardiac cycles.

Animal experiments have been performed and confirm that the moment parameter embodiments disclosed herein are highly effective classification parameters in order to discriminate between different types of arrhythmias, such as discriminate between hemodynamically stable and unstable arrhythmia and discriminate between arrhythmia origins, such as SVTs versus VTs. The classification between SVT and VT was conducted at a sensitivity of 81% and specificity of 100%. Correspondingly, the classification of arrhythmias as hemodynamically stable versus unstable resulted in a sensitivity of 93% and a specificity of 89%.

The defined time instance within the cardiac cycle that is employed to define the midpoint of the time window preferably coincides with a characteristic event or feature during the cardiac cycle. In an embodiment, the defined time instance corresponds to the timing of an R-wave during a cardiac cycle. The R-wave can be identified in the cardiac impedance signal itself but is preferably instead identified from the signal representative of the electric activity of the heart (IEGM signal) generated by the data acquisition unit 160. The impedance processor 131 then preferably identifies the impedance signal sample that coincides with the timing of the R-wave. This can easily be performed if the impedance processor 131 has access to the respective sampling frequencies of the IEGM signal and the cardiogenic impedance signal. Once the impedance sample that corresponds to the timing of the R-wave has been identified, the impedance processor 131 identifies the start or first impedance sample of the cardiogenic impedance signal within the time window and the last or end impedance sample within the time window.

The timing of the R-wave is particularly suitable as the defined time instance if the impedance vector employed for generating the cardiogenic impedance signal mainly reflects the ventricular contribution to the cardiogenic impedance. This means that the time window will then encompass those impedance samples that are generated during the period of main activity of the ventricles, i.e. the contraction of the ventricles during systole.

Correspondingly, if the impedance vector instead is selected so that the cardiogenic impedance signal mainly reflects the atrial contribution to the cardiogenic impedance, the defined time instance can advantageously coincide with the timing of the P-wave during a cardiac cycle. The P-wave can be identified in the cardiogenic impedance signal but is preferably identified from the IEGM signal generated by the data acquisition unit 160 in similarity to the detection of the R-wave as described above. The P-wave represents the depolarization of the atria and a time window centered at the impedance sample coinciding with the timing of the P-wave will therefore capture the mechanical activity of the atria, i.e. contraction of the atria during diastole.

The timings of the R-wave and the P-wave are easily identifiable from the IEGM signal but can also be detected from the cardiogenic impedance signal. Another cardiogenic feature that can be used for identifying the defined time instance and that is easily identifiable from the cardiogenic impedance signal is the global minimum in the cardiogenic impedance signal during systole. This minimum in the cardiogenic impedance signal, in particular if the impedance vector captures the ventricular contribution to the cardiogenic impedance, reflects the contraction of the ventricles during systole. Generally, the impedance minimum occurs close in time to the timing of the R-wave and therefore will result in comparative values for the moment parameter as compared to using the R-wave timing as defined time instance. In some applications and depending on the impedance vector, the impedance signal will be inverted so that a global maximum occurs close to the R-wave and coinciding with the ventricular contraction. For these applications, the timing of the global maximum in the cardiogenic impedance signal is instead used as defined time instance or the impedance signal values are first inverted before further processing.

A further embodiment that uses the signal representative of the electric activity from the data acquisition unit 160 for identifying the defined time instance would be to use the T-wave of the cardiac cycle.

The time window employed for identifying the relevant part of the cardiogenic impedance signal that is to be processed in order to calculate the moment parameter value is preferably larger than 100 ms and more preferably equal to or larger than 200 ms. Such a value is typically the lower limit in order to get sufficient number of impedance samples preceding and following the defined time instance constituting the midpoint of the time window. If a shorter time window would have been employed single odd values in the cardiogenic impedance signal occurring due other phenomena besides arrhythmia-related characteristics, such as movement of lead and electrodes slightly, can have a large (negative/undesired) impact on the moment parameter. Having sufficient number of impedance samples both prior and after the central midpoint reduces the effect of such oddities to the cardiogenic impedance signal.

The upper limit in terms of length of the time window is that it should be shorter then length of a cardiac cycle. This means that the impedance samples will not span over multiple complete cardiac cycles but will in clear contrast only contain a sub-portion of the impedance samples of a cardiac cycle if the (virtual) start of the cardiac cycle coincides with the start of the time window.

The time window can be fixed to thereby have a defined length in time. For instance, a time window of 300 ms has successfully been used in connection with the animal experiments described herein. Alternatively, the time window can be fixed in terms of encompassing a fixed number of impedance samples. In a preferred embodiment, the sampling frequency for generating the cardiogenic impedance signal is fixed so that these two alternatives are then equivalent.

In an alternative approach the length of the time window, either as defined in units of seconds or milliseconds or the number of including impedance samples, can be adaptive and preferably determined based on the current heart or cardiac rate. In such a case, a slower heart rate would mean a longer time window, whereas with a faster beating heart a comparatively shorter time window is preferably employed. The length of the time window can then be defined in terms of a function of the heart rate such as $$TimeWindow = f(HeartRate) = \alpha \times \frac{1}{HeartRate},$$

where $\alpha$ is a fixed positive factor smaller than one.

In a particular embodiment, the IMD 100 of FIG. 2 comprises an offset processor 135 that is configured to determine a minimum impedance amplitude for the cardiogenic impedance signal within the time window. This minimum impedance amplitude is marked as $A_{MIN}$ in FIG. 4. In such a case, the offset processor 135 can simply parse through all impedance samples within the time window and then notify the smallest amplitude value. The smallest amplitude value is regarded as an offset value and is preferably subtracted by the offset processor 135 from the amplitude values of all impedance samples encompassed by the time window. As a result of this offsetting the processed cardiogenic impedance signal will have a zero minimum for the relevant impedance samples within the time window. Thus, if an impedance sample has the impedance amplitude value A(i)' it will then have an updated amplitude value A(i)=A(i)'-$A_{MIN}$ following the subtraction. These updated amplitude values are then preferably employed by the moment processor 132 for calculating the moment parameter value as previously described.

The signal generator 150 and the signal sensing unit 155 of the IMD 100 can be configured to operate continuously or periodically in order to enable a continuous or periodic acquisition of the cardiogenic impedance signal. However, such a procedure generally drains quite a lot of power from the battery 180 of the IMD 100. Therefore, a preferred implementation embodiment in particular collects the cardiogenic impedance signal when there is a need thereof, i.e. in connection with an arrhythmia event.

The IMD 100 therefore preferably comprises an arrhythmia detector 134 configured to detect an arrhythmia of the heart. The arrhythmia detector 134 preferably performs this arrhythmia detection based on a heart rate of the heart as obtained from the IEGM signal from the data acquisition unit 160.

Thus, by continuously, periodically or intermittently monitoring the current heart rate of the patient using the IEGM signal, the arrhythmia detector 134 can detect whether an arrhythmia event is present or not. The arrhythmia detector 134 may also base the arrhythmia detection on further input information, such as data from an activity sensor (not illustrated) provided inside or connected to the IMD 100.

In such a case, the moment processor 132 is preferably responsive to the arrhythmia detector 134 and is configured to calculate the moment parameter value in response to the arrhythmia detector 134 detecting an arrhythmia event. Also the operation of the signal generator 150, the signal sensing unit 155 and the impedance processor 131 can be made responsive to the arrhythmia detector 134 detecting an arrhythmia event similar to a conditional operation of the moment processor 132.

The IMD 100 preferably comprises a shock generator 144 that is configured to generate a defibrillation/cardioversion shock that is to be applied to the heart using a shock electrode electrically connectable to the terminal 117 of the electrode connector 110. The operation of the shock generator 144 is controlled by the controller 130. The controller 130 then performs this control dependent on the arrhythmia classification of the arrhythmia classifier 133. As a consequence, a class-specific arrhythmia treatment is thereby achieved. For instance, an arrhythmia can be classified by the arrhythmia classifier 133 as being hemodynamically stable or unstable. In such a case, the controller 130 preferably activates the chock generator 144 to trigger generation and application of a shock if the arrhythmia classifier classifies an arrhythmia as a hemodynamically unstable arrhythmia. Correspondingly, if the arrhythmia classifier 133 instead classifies an arrhythmia as being hemodynamically stable, the controller 130 preferably prevents the shock generator 144 from generating and applying a shock. In this latter case no anti-arrhythmia treatment is applied to the heart. Alternatively, non-shock arrhythmia treatment, such as ATP, could instead be selected to be appropriate for the hemodynamically stable arrhythmia. The controller 130 then activates the ventricular pulse generator 143 and/or the atrial pulse generator 140 to generate and apply the ATP to the heart using electrodes selected by the controller 130 through control of the switch 120.

Correspondingly, if the arrhythmia classifier 133 is capable of classifying an arrhythmia as being a SVT or a VT, the operation of the shock generator 144 can be controlled by the controller 130 based on the classification result from the arrhythmia classifier 133. In a preferred implementation, the controller activates the shock generator 144 to generate and apply a shock if the arrhythmia classifier 133 classifies the arrhythmia as a VT. If the arrhythmia classifier 133 instead classifies the arrhythmia as a SVT, the controller 130 preferably prevents the shock generator 144 from generating and applying a shock to combat the arrhythmia. In comparison to above, no anti-arrhythmia therapy is applied at all to combat the SVT or a non-shock anti-arrhythmia treatment scheme, such as ATP, is instead selected by the controller 130.

Classification of an arrhythmia as hemodynamically stable versus unstable and SVT versus VT can of course be combined. Thus, a SVT or VT can be classified as a hemodynamically stable or unstable SVT or VT.

The arrhythmia classification based on the moment parameter by the arrhythmia classifier 133 is preferably conducted based on a comparison of the moment parameter with a threshold. Thus, the arrhythmia is classified as a type 1 arrhythmia or a type 2 based on whether the moment parameter exceeds or is smaller than the threshold.

The particular threshold employed in the preferred comparison by the arrhythmia classifier 132 can be generic or patient-specific. In the former case, the moment parameter value is calculated for different arrhythmia events in a patient population. Information from the patients and/or diagnostic data collected in connection with the arrhythmia events is then utilized by a physician in order to try to classify the arrhythmia as correctly as possible. In such a case, data from this whole patient population can be utilized in order to derive a generic threshold that can be programmed into the IMD, such as transmitted to the transceiver 190 and stored in a memory 170 accessible to the arrhythmia classifier 133. In an alternative approach, the threshold is a patient-specific threshold. In such a case, information from the patient and/or diagnostic data collected in connection with the arrhythmia events is utilized by a physician in order to classify the arrhythmia events as in above. The difference now is that the data originates from a single patient. Valuable data that can be used for determining patient specific thresholds can be collected at the time of implantation of the IMD 100. Today arrhythmias are sometimes triggered when implanting the IMD 100 in order to verify that the IMD 100 correctly detects the arrhythmia and initiates a pre-programmed anti-arrhythmia treatment. The moment parameter value can then be determined during these triggered arrhythmia events in order to define a suitable value for the threshold.

The threshold does not necessarily have to be a static value but can instead be dynamically adjusted and tuned in order to derive as a correct threshold value as possible. The IMD 100 can, for instance, be programmed to derive the moment parameter for the first X detected arrhythmia events. The moment parameter values for these first X arrhythmias are then not employed in order to select appropriate anti-arrhythmia treatment but are instead utilized in order to calculate a suitable threshold. The moment parameter values calculated by the moment processor 132 for these X arrhythmias are preferably uploaded by the transceiver 190 to the data processing unit of the physician. The physician uses the received data together with other patient data from the IMD 100 and/or from the patient himself/herself in order to try to classify the arrhythmias and find an appropriate threshold. The determined threshold is then downloaded to the IMD 100 and can be utilized in arrhythmia classification by the arrhythmia classifier 132 for any following arrhythmias in the patient. The parameter X can be pre-programmed in the IMD or determined by the physician. Generally, a value of 5-10 should be sufficient in order to get enough data to determine an accurate threshold.

A generic threshold can also be tuned to be more patient specific. In such a case, the IMD 100 is initially programmed to use a generic threshold determined for a patient population. Moment parameter values are then determined for some detected arrhythmia events and information of these interval parameters are transmitted by the IMD 100 to the data processing unit. There the physician can investigate, based on other diagnostic data from the IMD 100 and/or from the patient, whether the default threshold needs to be adjusted or tuned to be more accurate for the specific patient.

In an embodiment, the moment processor 132 is configured to generate respective moment parameter values for multiple, preferably multiple consecutive, cardiac cycles. The arrhythmia classifier 133 then preferably classifies an arrhythmia based on these multiple moment parameter values.

The arrhythmia classifier 133 can then use a discrimination window that defines a number of consecutive cardiac cycles or a time length. In the former case, respective moment parameter values are determined for this number of cardiac cycles and in the latter case for the consecutive cardiac cycles that fall within the time length.

Each of the respective moment parameter values is preferably compared to the previously discussed threshold and thereby generates an arrhythmia classification. The numbers of arrhythmia classifications according to the first type and the second type, respectively, are determined for the discrimination window. In a first embodiment, the arrhythmia type that was most common for the discrimination window is then selected by the arrhythmia classifier 133 as the conclusive arrhythmia class for that discrimination window. For instance, if 32 cardiac cycles are classified as SVT and 14 as VT from the onset of the arrhythmia until time out of the discrimination window, then the total episode could be classified as an SVT episode.

In an alternative approach, the number of cardiac cycles of the discrimination window that is classified according to one of the types or classes must reach a defined proportion of the total number of cardiac cycles for definitive classification. For instance, at least 60% of the cardiac cycles tested during the discrimination window needs to be classified by the arrhythmia classifier 133 to belong to the same arrhythmia class in order to classify the episode as being of that arrhythmia class.

If the number of cardiac cycles belonging to each class is identical according to the first embodiment above or whether the defined proportion of cardiac cycles is not exceeded for any of the arrhythmia classes according to the second embodiment various techniques can be taken by the IMD 100. In an embodiment, the arrhythmia classifier 133 automatically selects a defined default arrhythmia class, such as hemodynamically unstable arrhythmia or VT. The IMD 100 will then select an appropriate anti-arrhythmia scheme suitable for this default arrhythmia class, typically generation and application of a shock by the shock generator 144. In alternative embodiments, the discrimination window is either extended or restarted in order to try to classify the arrhythmia with sufficient certainty.

Animal studies have been conducted to verify that embodiments can be used to correctly classify arrhythmias induced in the test animals. The study was conducted on nine porcine. The animals were implanted with two pacemaker/ICD leads in the right atrium, two in the right ventricle and one in a left lateral coronary vein. An ICD can was also implanted in a pectoral position.

The first set of RA and RV leads was used to stimulate the heart very quickly in order to simulate a cardiac arrhythmia. Ventricular, supraventricular, hemodynamically stable and hemodynamically unstable arrhythmias were created.

Impedance data was measured from the second set of RA and RV leads and the LV lead in various configurations and the data was processed as disclosed herein in order to calculate the moment parameter.

In the experiments the impedance between two electrodes is measured by emitting small current pulses at a frequency of 128 Hz. The current pulses are preferably charge neutral and can, for instance, consist of a first negative pulse having a first duration, followed by a positive pulse having half the first duration and followed by a second negative pulse having the first duration. If the (positive) amplitude of the positive pulse is four times the (negative) amplitude of the two negative pulses charge neutrality is achieved. Examples of amplitudes that can be used include +250 µA and +750 µA for the positive pulse and −62.5 µA and −187.5 µA for the negative pulses. The pulse duration for the positive pulse can advantageously be in the interval of from 14 to 19 µs. The above presented example of current pulses should merely be seen as illustrative and non-limiting examples.

The resulting voltage is measured by a pair of electrodes. From the measured voltage signal and the emitted current pulses, the impedance between the voltage sensing electrodes is calculated by dividing the area of the measured voltage pulse by the area of the emitted current pulse.

The impedance signal is then high pass filtered to remove the DC component that is present and to amplify the beat-to-beat variations in the signal. The filter used in the experiment had cutoff frequencies of 0.55 and 64 Hz. The resulting cardiogenic impedance signal is then processed as disclosed herein in order to derive the arrhythmia classification parameter, i.e. moment parameter.

Figure 7:
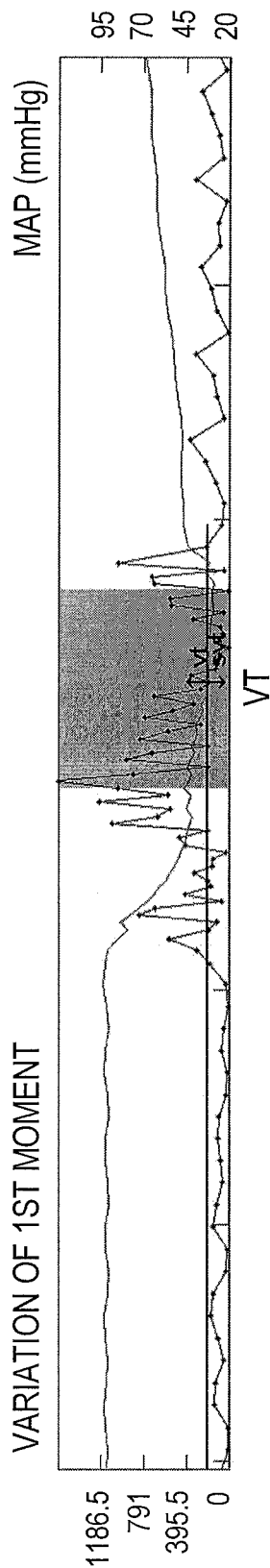
FIG. 7 schematically illustrates a moment parameter representing the variation of the first moment and mean arterial pressure (MAP) over time for a porcine suffering from various forms of arrhythmias as recorded with a right atrial bipolar impedance vector.

FIG. 5 displays an embodiment of the moment parameter in the form of the first moment for RV tip—RV ring bipolar impedance vector. In FIGS. 5-7 a moment parameter is plotted together with the mean arterial pressure (MAP) over time. The MAP is represented by the continuous line and the moment parameter is the continuous line with dots. The length of a test episode is marked with gray. It is clearly seen from the figure that the moment parameter can be utilized to accurately classify arrhythmias as hemodynamically stable or unstable, SVT or VT through a threshold comparison.

FIG. 6 schematically illustrates a moment parameter representing the second moment and MAP over time for a porcine suffering from various forms of arrhythmias as recorded with a RV tip—RV ring bipolar impedance vector.

FIG. 7 schematically illustrates a moment parameter representing the variation of the first moment and MAP over time for a porcine suffering from various forms of arrhythmias as recorded with a RA bipolar impedance vector.

FIGS. 5 to 7, hence, clearly illustrates animal experiments where various embodiments of the moment parameter have been determined for various impedance vectors and still being able to accurately classify different induced arrhythmias.

The controller 130 is further coupled to a memory 170 by a suitable data/address bus, wherein the programmable operating parameters used by the controller 130 are stored and modified, as required, in order to customize the operation of the IMD 100 to suit the needs of a particular patient. Such operating parameters define, for example, time threshold, pacing pulse amplitude, pulse duration, electrode polarity, rate, sensitivity, automatic features, and time interval between pacing pulse of an applied pacing pulse sequence.

The memory 170 may also advantageously store diagnostic data collected by the IMD 100. The diagnostic data include the IEGM signal from the data acquisition unit 160, the cardiogenic impedance signal from the impedance processor 131 and the classification data, including final classification from the arrhythmia classifier 133 and the moment parameter value from the moment processor 132.

Advantageously, the operating parameters of the IMD 100 may be non-invasively programmed into the memory 170 through a transceiver 190 in communication via a communication link with the previously described communication unit of the programmer. The controller 130 activates the transceiver 190 with a control signal. The transceiver 190 can alternatively be implemented as a dedicated receiver and a dedicated transmitter connected to separate antennas or a common antenna, preferably a radio frequency (RF) antenna 195.

The IMD 100 additionally includes a battery 180 that provides operating power to all of the circuits shown in FIG. 2.

In the figure the impedance processor 131, the moment processor 132, the arrhythmia classifier 133, the arrhythmia detector 134 and the optional offset processor 135 have been exemplified as being run by the controller 130.

These units can then be implemented as a computer program product stored on the memory 170 and loaded and run on a general purpose or specially adapted computer, processor or microprocessor, represented by the controller 130 in the figure. The software includes computer program code elements or software code portions effectuating the operation of the impedance processor 131, the moment processor 132, the arrhythmia classifier 133, the arrhythmia detector 134 and the offset processor 135. The program may be stored in whole or part, on or in one or more suitable computer readable media or data storage means that can be provided in an IMD 100.

In an alternative embodiment, the impedance processor 131, the moment processor 132, the arrhythmia classifier 133, the arrhythmia detector 134 and the offset processor 135 are implemented as hardware units either forming part of the controller 130 or provided elsewhere in the IMD 100.

Figure 8:
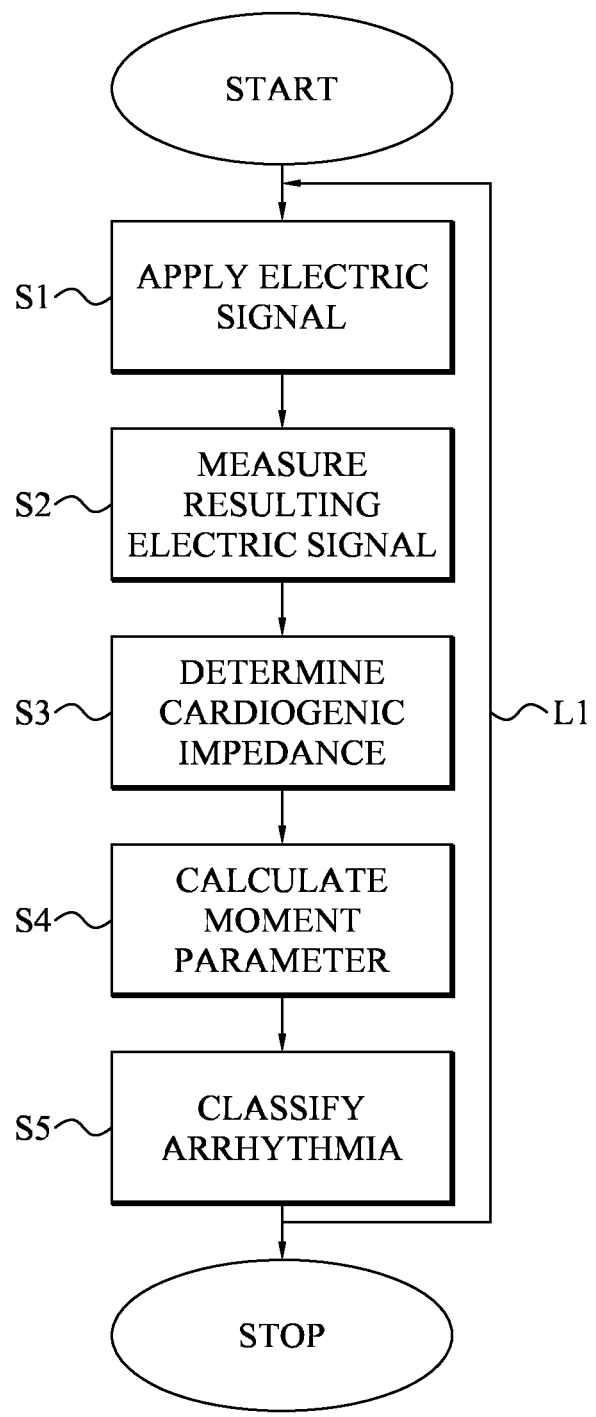
FIG. 8 is a flow diagram illustrating a method of classifying arrhythmia according to an embodiment.

FIG. 8 is a flow diagram illustrating a method for classifying an arrhythmia of a heart of an animal subject, preferably a mammalian subject and more preferably a human subject. The method involves generating and applying an electric signal is applied in step S1 over a portion of the heart and sensing the resulting electric signal in step S2 over a portion of the heart. A next step S3 determines a cardiogenic impedance signal based on information of the electric signal applied in step S1 and the resulting electric signal measured in step S2. The cardiogenic impedance signal is processed in step S4 in order to calculate the moment parameter representative of a weighted sum of impedance amplitudes within a time window centered at a defined time instance within a cardiac cycle and where the respective weights are dependent on the length in time between the defined time instance and the impedance sample carrying the impedance amplitude value associated with the given weight. The moment parameter calculated in step S4 is utilized in step S5 to classify a detected arrhythmia as either a type 1 or a type 2 arrhythmia.

The arrhythmia classification of step S5 is preferably performed based on the moment parameter values of multiple, preferably consecutive, cardiac cycles, which is schematically illustrated by the line L1.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical device for delivering cardiac therapy to a heart of a subject comprising:
   an electrode connector electrically connectable to multiple electrodes of which at least one is arranged on a cardiac lead electrically connected to said electrode connector;
   a signal generator connected to said electrode connector and configured to generate an electric signal applicable over two electrodes of said multiple electrodes;
   a signal sensing unit connected to the electrode connector and configured to sense a resulting electric signal over two electrodes of said multiple electrodes;
   an impedance processor configured to determine a cardiogenic impedance signal for at least a portion of a cardiac cycle based on said electric signal generated by said signal generator and said resulting electric signal sensed by said signal sensing unit;
   a moment processor configured to calculate, based on said cardiogenic impedance signal determined by said impedance processor, a moment parameter value representative of a weighed sum of impedance amplitudes within a time window encompassed by said at least a portion of said cardiac cycle and centered at a defined time instance within said at least a portion of said cardiac cycle, wherein each respective weight is dependent on a length in time between said defined time instance and the point in time for the impedance amplitude associated with said each respective weight; and
   an arrhythmia classifier configured to classify an arrhythmia of said heart based on said moment parameter value calculated by said moment processor.

2. The device according to claim 1, wherein said moment processor is configured to calculate, based on said cardiogenic impedance signal determined by said impedance processor, said moment parameter value based on $$\sum_i r(i)^k \times A(i),$$

wherein r(i) represents the length in time between said defined time instance and the point in time for impedance sample number i of said cardiogenic impedance signal, A(i) represents the impedance amplitude for said impedance sample number i, k is a positive integer and i∈[α, β], where α is the sample number of a first impedance sample within said time window and β is the sample number of a last impedance sample within said time window.

3. The device according to claim 2, wherein said moment processor is configured to calculate, based on said cardiogenic impedance signal determined by said impedance processor, said moment parameter value as $$P = \sum_i r(i) \times A(i).$$

4. The device according to claim 2, wherein said moment processor is configured to calculate, based on said cardiogenic impedance signal determined by said impedance processor, said moment parameter value as $$P = \sum_i r(i)^2 \times A(i).$$

5. The device according to claim 2, wherein said moment processor is configured to calculate, based on said cardiogenic impedance signal determined by said impedance processor, said moment parameter value as $$P = \frac{\sum_i r(i) \times A(i)}{\sum_i A(i)}.$$

6. The device according to claim 1, wherein said impedance processor is configured to determine said cardiogenic impedance signal to comprise a respective impedance amplitude for each impedance sample within said at least a portion of a cardiac cycle based on said electric signal generated by said signal generator and said resulting electric signal sensed by said signal sensing unit.

7. The device according to claim 1, further comprising a data acquisition unit connected to said electrode connector and configured to generate a signal representative of electric activity of at least a portion of said heart, wherein said moment processor is configured to identify said defined time instance based on said signal representative of said electric activity.

8. The device according to claim 7, wherein said moment processor is configured to identify said defined time instance as the time instance of an R-wave or a P-wave of said cardiac cycle based on said signal representative of said electric activity.

9. The device according to claim 7, further comprising an arrhythmia detector configured to detect an arrhythmia of said heart based on a heart rate of said heart obtained from said signal representative of said electric activity generated by said data acquisition unit.

10. The device according to claim 9, wherein said moment processor is responsive to said arrhythmia detector detecting said arrhythmia and is configured to calculate said moment parameter in response to said arrhythmia detector detecting said arrhythmia.

11. The device according to claim 7, wherein said moment processor is configured to determine a length of said time window based on a heart rate of said heart obtained from said signal representative of said electric activity generated by said data acquisition unit.

12. The device according to claim 1, wherein said arrhythmia classifier is configured to compare said moment parameter value to a threshold and classify said arrhythmia based on said comparison.

13. The device according to claim 1, further comprising an offset processor configured to determine a smallest impedance amplitude for said cardiogenic impedance signal within said time window and subtract said smallest impedance amplitude from said impedance amplitudes within said time window before said moment processor calculates said moment parameter value.

14. The device according to claim 1, wherein said arrhythmia classifier is configured to classify said arrhythmia as being a hemodynamically stable arrhythmia or a hemodynamically unstable arrhythmia based on said moment parameter value calculated by said moment processor.

15. The device according to claim 14, further comprising:
a shock generator connected to said electrode connector and configured to generate a defibrillation shock applicable to at least a portion of said heart; and
a controller connected to said shock generator and configured to activate said shock generator if said arrhythmia classifier classifies said arrhythmia as a hemodynamically unstable arrhythmia and prevent said shock generator from generating said defibrillation shock if said arrhythmia classifier classifies said arrhythmia as a hemodynamically stable arrhythmia.

16. The device according to claim 1, wherein said arrhythmia classifier is configured to classify said arrhythmia as being a supraventricular tachycardia or ventricular tachycardia based on said moment parameter value calculated by said moment processor.

17. The device according to claim 16, further comprising:
a shock generator connected to said electrode connector and configured to generate a defibrillation shock applicable to at least a portion of said heart; and
a controller connected to said shock generator and configured to activate said shock generator if said arrhythmia classifier classifies said arrhythmia as a ventricular tachycardia and prevent said shock generator from generating said defibrillation shock if said arrhythmia classifier classifies said arrhythmia as a supraventricular tachycardia.

18. The device according to claim 1, wherein
said moment processor is configured to calculate, based on said cardiogenic impedance signal determined by said impedance processor, multiple respective moment parameter values for multiple cardiac cycles; and
said arrhythmia classifier is configured to classify said arrhythmia of said heart based on said multiple respective moment parameter values calculated by said moment processor.

19. The device according to claim 18, wherein said arrhythmia classifier is configured to compare said multiple respective moment parameter values to a threshold and classify said arrhythmia as being of a first arrhythmia type if a pre-defined number of said multiple respective moment parameter values exceed said time threshold and classify said arrhythmia as being of a second arrhythmia type if a pre-defined number of said multiple respective moment parameter values is below said time threshold.

20. The device according to claim 1, wherein said moment processor is configured to calculate, based on said cardiogenic impedance signal determined by said impedance processor, said each respective weight as a respective signed weight having a magnitude dependent on said length in time between said defined time instance and said point in time for said impedance amplitude associated with said each respective weight and a sign dependent on whether said point in time for said impedance amplitude associated with said each respective weight occurs prior or after said defined time instance.

21. A method for classifying an arrhythmia of a heart of a subject comprising:
applying an electric signal over a portion of said heart;
sensing a resulting electric signal over a portion of said heart;
determining a cardiogenic impedance signal for at least a portion of a cardiac cycle based on said electric signal and said resulting electric signal;
calculating, based on said cardiogenic impedance signal, a moment parameter value representative of a weighed sum of impedance amplitudes within a time window encompassed by said at least a portion of said cardiac cycle and centered at a defined time instance within said at least a portion of said cardiac cycle, wherein each respective weight is dependent on a length in time between said defined time instance and the point in time for the impedance amplitude associated with said each respective weight; and
classifying an arrhythmia of said heart based on said moment parameter value.

* * * * *